United States Patent
Sumner, Jr. et al.

(10) Patent No.: US 6,265,608 B1
(45) Date of Patent: Jul. 24, 2001

(54) METHOD OF PURIFYING AROMATIC DICARBOXYLIC ACIDS

(75) Inventors: Charles E. Sumner, Jr.; Brent A. Tennant, both of Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/107,401

(22) Filed: Jun. 30, 1998

(51) Int. Cl.$^7$ .................................................. C07C 51/42
(52) U.S. Cl. ............................................ 562/485; 562/487
(58) Field of Search ..................................... 562/487, 485

(56) References Cited

U.S. PATENT DOCUMENTS

| | | | |
|---|---|---|---|
| 3,607,921 | * 9/1971 | Stancell et al. | 260/525 |
| 4,201,872 | 5/1980 | Kimura et al. | 562/487 |
| 4,394,299 | 7/1983 | Puskas et al. | 252/447 |
| 4,629,715 | 12/1986 | Schroeder | 502/185 |
| 4,833,269 | 5/1989 | Schroeder | 562/484 |
| 4,892,972 | 1/1990 | Schroeder et al. | 562/487 |
| 5,756,833 | * 5/1998 | Rosen et al. | 562/486 |

FOREIGN PATENT DOCUMENTS

WO 94/20447   9/1994   (WO) ........................... C07C/51/487

* cited by examiner

Primary Examiner—Rosalynd Keys
(74) Attorney, Agent, or Firm—Harry J. Gwinnel; Matthew W. Smith

(57) ABSTRACT

An aromatic dicarboxylic acid is purified by oxidizing m-xylene or p-xylene to produce crude isophthalic acid or crude terephthalic acid, respectively. The products of the oxidizing step are hydrogenated in the presence of a palladium catalyst. Carbon monoxide is introduced during the hydrogenation step. The palladium catalyst is provided on a carbon substrate. The products of the oxidizing step are dissolved in a solvent, which may be water, prior to the hydrogenation step. The products of the oxidizing step may be dissolved at an elevated temperature, above the normal boiling point of the solvent. The oxidation step produces isophthalic acid, 3-carboxybenzaldehyde and fluorenones in the case of oxidizing m-xylene and produces terephthalic acid, 4-carboxybenzaldehyde and fluorenones in the case of oxidizing p-xylene. It may be helpful to monitor the disappearance of 3-carboxybenzaldehyde in the case of oxidizing m-xylene and 4-carboxybenzaldehyde in the case of oxidizing pxylene, and reducing the amount of carbon monoxide when the rate of disappearance is below a predetermined minimum. After the hydrogenation step, the isophthalic acid or terephthalic acid may be crystallized. The carbon monoxide may be maintained at a concentration of 100 to 500 ppm based on added hydrogen and carbon monoxide. Other aromatic dicarboxylic acids may also purified by this procedure.

61 Claims, No Drawings

METHOD OF PURIFYING AROMATIC DICARBOXYLIC ACIDS

BACKGROUND OF THE INVENTION

1. Field of the Invention

The present invention relates in general to purifying aromatic dicarboxylic acids and more specifically to improving catalyst selectivity during aromatic dicarboxylic acid purification such that the aromatic dicarboxylic acid product is not hydrogenated.

2. Description of the Related Art

Aromatic dicarboxylic acids are used to produce a variety of polyester products. Aromatic dicarboxylic acids are generally synthesized by the catalytic oxidation of the corresponding aromatic dialkyl compound. For example, terephthalic acid (TPA) and isophthalic acid (IPA) are produced by the liquid phase oxidation of p-xylene and m-xylene, respectively, by the following reactions.

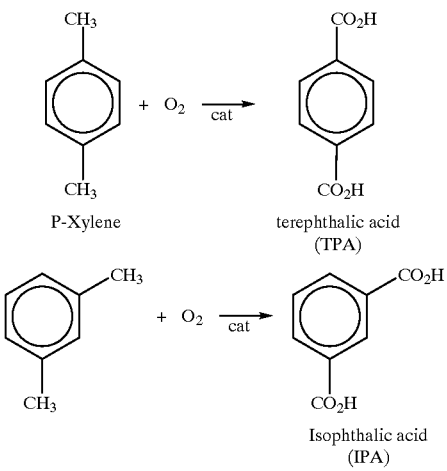

In the above reactions, Co/Mn/Br may be used as the catalyst. The above reactions work well. However, in addition to producing the aromatic dicarboxylic acids, a number of impurities are also produced. The following are the impurities produced in the catalytic oxidation of isophthalic acid:

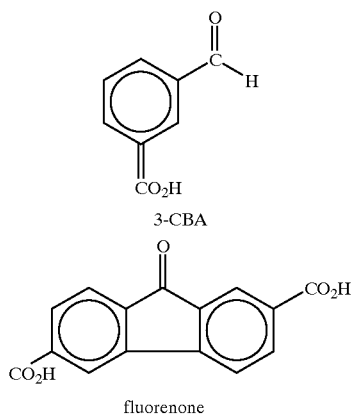

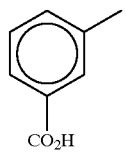

m-toluic acid

Carboxybenzaldehyde (CBA) and toluic acid result from the incomplete oxidation of the aromatic dimethyl compound. In the oxidation of m-xylene to produce IPA, 3-CBA is produced. In the oxidation of p-xylene to produce TPA, 4-CBA is produced. Likewise, m-toluic acid is an impurity in IPA production and P-toluic acid is an impurity in TPA production. Because neither the CBA nor the toluic acid have two carboxylic acid groups, both would terminate the chain of a polyester produced from a crude dicarboxylic acid. Thus, both CBA and toluic acid are undesirable. However, toluic acid is only produced in small quantities and is water soluble, thus removable in a crystallization step.

In addition to the CBA and toluic acid impurities, compounds generally known as "fluorenones" are produced. The fluorenone shown above is only one of several isomers. Fluorenones have two carboxylic acid groups, and are therefore not chain terminating. However, fluorenones are yellow. Thus, if fluorenones are present, the polyester produced from the aromatic dicarboxylic acid will appear dingy.

In view of the foregoing, it is necessary to purify crude aromatic dicarboxylic acids. The dicarboxylic acids are purified by catalytic hydrogenation of the impurities in the following reactions.

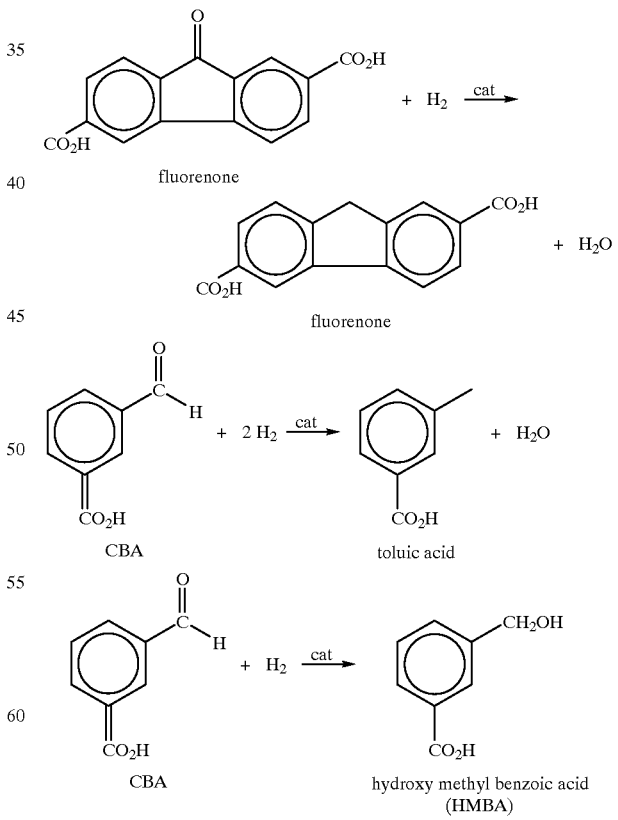

As can be seen above, fluorenones are converted to "fluorenes", and CBAs are converted to toluic acid and hydroxymethylbenzoic acid (HMBA). Fluorenes are bifunctional, thus not polymer chain terminating, and are white. The purification is generally carried out by dissolving the oxidation products in water at an elevated temperature and pressure, followed by contacting the resulting solution with a bed of hydrogenation catalysts in the presence of a partial pressure of hydrogen. The product mixture is allowed to cool which causes the purified product to crystallize. The toluic acid and HMBA remain in solution. The hydrogenation catalyst is commonly palladium on a carbon (charcoal) support, which catalyst contains 0.5 weight percent palladium.

One of the disadvantages of the purification process is the tendency to hydrogenate the aromatic dicarboxylic acid to produce undesired by-products. In the production of CBA, the following undesired hydrogenation reactions may occur.

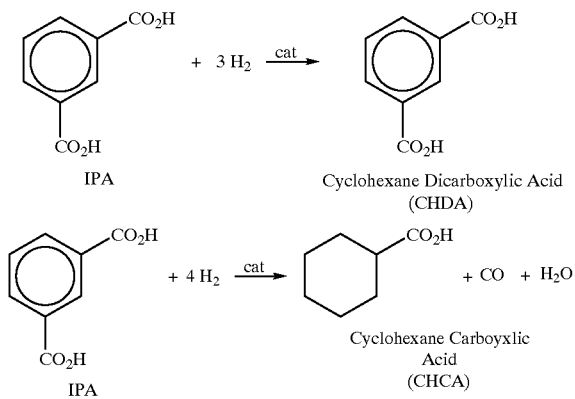

As can be seen, IPA may be hydrogenated to cyclohexane dicarboxylic acid (CHDA) and cyclohexane carboxylic acid (CHCA). Only a small amount of CHCA is produced. IPA may also be hydrogenated to m-toluic acid, but little m-toluic acid is produced on this route. Note that benzoic and toluic acids may also be produced from CBA. The by-products are water soluble, and thus are not overly difficult to remove. However, the by-products represent a yield loss of the desired bromate dicarboxylic acid.

Most past efforts aimed at decreasing the amount of excess CHDA and CHCA produced during the purification centered around the addition of rhodium to the palladium/carbon catalyst, which is typically used in the purification process. For example, U.S. Pat. No. 4,394,299 teaches the use of a by-metallic Pd/Rh-on-carbon catalyst for the purification of terephthalic acid to decrease the amount of 4-CBA and minimize the amount of CHDA byproduct. U.S. Pat. Nos. 4,629,715 and 4,892,972 teach the use of layered catalyst beds consisting of a layer of Rh/C catalyst before or after the bulk of Pd/C catalysts. However, rhodium is very expensive.

SUMMARY OF THE INVENTION

Accordingly, it is an object of the present invention to purify aromatic dicarboxylic acids to eliminate chain terminating by-products and eliminate yellow fluorenones.

It is a further object of the present invention to catalytically hydrogenate the impurities of the oxygenation of a dialkyl aromatic while minimizing the generation of by products.

It is a still further object of the present invention to minimize the hydrogenation of the dicarboxylic acid desired product without decreasing the rate of hydrogenation of impurities such as CBA and color bodies.

It is another object of the present invention to purify aromatic dicarboxylic acid while avoiding the use of expensive rhodium catalysts.

These together with other objects are accomplished by providing a method for purifying aromatic dicarboxylic acids which oxidizes m-xylene or p-xylene to produce crude isophthalic acid or crude terephthalic acid, respectively. The products of the oxidizing step are hydrogenated in the presence of a palladium catalyst. Carbon monoxide is introduced during the hydrogenation step. The palladium catalyst is provided on a carbon substrate. The products of the oxidizing step are dissolved in a solvent, which may be water, prior to the hydrogenation step. The products of the oxidizing step may be dissolved at an elevated temperature, above the normal boiling point of the solvent. The oxidation step produces isophthalic acid, 3-carboxybenzaldehyde and fluorenones in the case of oxidizing m-xylene and produces terephthalic acid, 4-carboxybenzaldehyde and fluorenones in the case of oxidizing p-xylene. The step may include the step of monitoring the disappearance of 3-carboxybenzaldehyde in the case of oxidizing m-xylene and 4-carboxybenzaldehyde in the case of oxidizing p-xylene, and reducing the carbon monoxide when the rate of disappearance is below a predetermined minimum. The hydrogenation step hydrogenates the 3-carboxybenzaldehyde to m-toluic acid and 3-hydroxymethyl benzoic acid in the case of oxidizing m-xylene and hydrogenates the 4-carboxybenzaldehyde to p-toluic acid and 4-hydroxymethyl benzoic acid in the case of oxidizing p-xylene. After the hydrogenation step, the isophthalic acid or terephthalic acid may be crystallized. The carbon monoxide may be maintained at a concentration of 10 to 1000 ppm based on added hydrogen and carbon monoxide, and preferably maintained at 100 to 500 ppm. Other aromatic carboxylic acids may also purified by this procedure.

DETAILED DESCRIPTION OF THE PREFERRED EMBODIMENTS

The invention will now be described with reference to the following detailed description and Examples which are given by way of illustration only, not limitation. According to a preferred embodiment, the products of an oxidation reaction of a dialkyl aromatic are hydrogenated in the presence of a palladium catalyst in a liquid phase reaction. The reaction by-products are dissolved in a solvent, such as water. If water is used as the solvent, the water must be heated to ensure dissolution of the products of the oxidation reaction. For example, in producing IPA, water is heated to approximately 230° C., and in producing TPA, water is heated to approximately 260° C. Of course, at these temperatures, the water is above its normal boiling point, and thus dissolution occurs under pressure. The amount of oxidation product which can be combined in the solvent will, of course, vary from solvent to solvent. However, for water, the oxidation product-water mixture contains approximately 20 weight percent oxidation product.

The hydrogenation catalyst is commonly palladium on a carbon (charcoal) support, which catalyst contains 0.5 weight percent palladium. Other supports can also be used. For example, palladium on a $TiO_2$ support is suitable.

The hydrogenation is performed using a partial pressure of hydrogen gas such that hydrogen goes into solution. The partial pressure of hydrogen may be 10–100 psi absolute.

Carbon monoxide is added to the hydrogen feed gas to preserve the aromatic dicarboxylic acid. That is, by adding carbon monoxide to the hydrogen feed gas, hydrogenation of the aromatic dicarboxylic acid is suppressed such that hydrogenated by-products are reduced. The addition of carbon monoxide has little effect on the elimination of fluorenone color bodies or chain terminating incomplete oxidation products, such as CBA. The amount of carbon monoxide used in the feed gas varies from about 10 ppm based on $H_2$+CO to 1000 ppm. Preferably, the amount of CO should be within the range of 100 to 500 ppm.

The present invention works with any aromatic dicarboxylic acid, but is especially useful in the purification of isophthalic acid (IPA) and terephthalic acid (TPA). Referring to Table 1, examples 1–7 demonstrate that the addition of small amounts of CO, typically 100 ppm to 500 ppm, serve to decrease the amount of CHDA produced from over hydrogenation, while not effecting the desired hydrogenation of CBA. In each of examples 1–6, a one gallon titanium autoclave equipped with a drop in catalyst basket and a bottom mounted flush valve was charged with 1400 grams of water and 250 grams of crude IPA containing 800 ppm 3-CBA.

TABLE I

| Example | $H_2$ press psi | CO ppm | $k_{[CHDA]}(min^{-1})$ (X $10^{-4}$) | $k_{[CBA]}$ (min$^{-1}$) |
|---|---|---|---|---|
| 1 | 100 | | 1.2 | 0.108 |
| 2 | 100 | 100 | 0.5 | 0.102 |
| 3 | 100 | 500 | 0.0 | 0.044 |
| 4 | 300 | | 2.1 | 0.085 |
| 5 | 300 | 100 | 1.9 | 0.100 |
| 6 | 300 | 500 | 0.8 | 0.116 |
| 7 | 100 | 500 | 0.007 | 0.046 |

For examples 1–6, the autoclave was sealed and heated to 230° C. while agitating the mixture. Then, $H_2$ was introduced to reach the various partial pressures listed in Table 1. In examples 2 and 5, the $H_2$ contained 100 ppm CO, and in examples 3, 6 and 7, the $H_2$ contained 500 ppm CO. Before the catalyst was dropped into the autoclave, a T=0 sample was taken through the flush valve. At this point, the catalyst basket was dropped into the mixture. The catalyst basket contained 2 grams of a palladium/carbon catalyst containing 0.5 weight percent palladium. Samples were taken from the flush valve at 10, 20, 40, 60 and 90 minutes. These samples were evaporated to dryness and analyzed for hydroxymethyl benzoic acid, toluic acid, 3-CBA, benzoic acid, cis and trans 3-CHDA and IPA. The first order rate constants for the disappearance of 3-CBA and the appearance of 3-CHDA were calculated from log plots. Example 7 relates to the purification of TPA. For example 7, crude TPA was dissolved at a temperature of 260° C. with other conditions being the same.

As can be seen by comparing the rate constants for the appearance of CHDA in Table 1, the addition of small amounts of carbon monoxide in examples 2, 3 and 5–7 significantly decreases the amount of undesired CHDA produced when compared to examples 1 and 4 in which no CO is used. As more CO is used, the production rate of CHDA decreases. Compare examples 2 and 3 and examples 5 and 6.

In example 3, when 500 ppm of CO is introduced with a $H_2$ partial pressure of 100 psi, the rate constant for producing CHDA was 0.0. However, for example 3, the rate constant for the disappearance of CBA decreased to 0.044. Thus, perhaps too much CO was used in example 3. On the other hand, in example 6, 500 ppm of CO was also used. However, comparing examples 4–6, it can be seen that the rate of disappearance of the CBA impurity was highest in example 6 (116), which used more CO than Examples 4 or 5. Both examples 3 and 6 use the same concentration of CO, 500 ppm, but example 6 has a greater $H_2$ partial pressure. Table 1, therefore, demonstrates that if the $H_2$ partial pressure is increased, it is acceptable to use more carbon monoxide. The results shown in Table 1 clearly indicate that the addition of small amounts of CO to the purification of aromatic dicarboxylic acids significantly decreases the production of undesired by-products.

In example 3, the elimination of CBA was decreased by 59%. Thus, although small amounts of carbon monoxide are desirable, too much carbon monoxide is not good. The exact reason for this is not completely understood. However, how much carbon monoxide is too much depends on the hydrogen pressure. The carbon monoxide may bond to a portion of the hydrogenation cites on the palladium. The oxidation impurities (such as CBA, toluic acid and fluorenones) may be more easily hydrogenated than IPA and TPA. In this case, the addition of small amounts of carbon monoxide would not greatly affect the hydrogenation of the oxidation impurities. However, because IPA and TPA are less easily hydrogenated, the addition of small amounts of CO, would decrease the hydrogenation of IPA and TPA.

There are several ways to control the amount of carbon monoxide added to the process. For example, a large amount of carbon monoxide could be added when the catalyst bed is fresh. It has been demonstrated that a fresh catalyst bed more easily hydrogenates aromatic dicarboxylic acids. After the initial addition of CO, the hydrogenation products could be monitored. When the rate of disappearance of CBA begins to decrease, this may indicate that too many sites on the catalyst have been poisoned. At this point, the feed of carbon monoxide is decreased, or the carbon monoxide source is simply removed.

The deactivation of the catalyst toward the desired dicarboxylic acid is reversible. That is, after removal or decreasing the carbon monoxide source, the catalyst will become reactivated. It is important to monitor this reactivation to ensure that hydrogenation of the aromatic carboxylic acid IPA or TPA does not occur. To this end, the CBA concentration may be monitored. After disappearance of CBA reaches an acceptable rate, the carbon monoxide feed may be increased or, if the carbon monoxide feed was removed entirely, the CO feed may be reintroduced. Of course, the CO feed could eventually be stabilized to the desired concentration such that, is it not necessary to change the CO feed rate.

The many features and advantages of the invention are apparent from the detailed specification and, thus, it is intended by the appended claims to cover all such features and advantages of the invention which fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:
1. A method of purifying an aromatic dicarboxylic acid, comprising the steps of:
   oxidizing a dialkylaromatic to a crude aromatic dicarboxylic acid to produce aromatic dicarboxylic acid-color bodies and an aromatic carboxylic acid aldehyde;
   contacting the products of the oxidizing step with hydrogen in the presence of a palladium catalyst;
   introducing carbon monoxide during the hydrogenation step, the amount of carbon monoxide introduced being less than or equal to 1000 ppm based on the added hydrogen and carbon monoxide; and monitoring the disappearance of the acid aldehyde and reducing the carbon monoxide introduction when the rate of disappearance is below a predetermined minimum.

2. A method of purifying an aromatic dicarboxylic acid according to claim 1, wherein the palladium catalyst is provided on a carbon substrate.

3. A method of purifying an aromatic dicarboxylic acid according to claim 1, wherein the products of the oxidizing step are dissolved in a solvent prior to the hydrogenation step.

4. A method of purifying an aromatic dicarboxylic acid according to claim 3, wherein water is used as the solvent.

5. A method of purifying an aromatic dicarboxylic acid according to claim 3, wherein the products of the oxidizing step are dissolved in a solvent at an elevated temperature, above the normal boiling point of the solvent.

6. A method of purifying an aromatic dicarboxylic acid according to claim 1, wherein the hydrogenation step hydrogenates the aromatic carboxylic acid aldehyde to an aromatic alkyl carboxylic acid and an aromatic alcohol carboxylic acid.

7. A method of purifying an aromatic dicarboxylic acid according to claim 1, wherein the carbon monoxide is introduced intermittently during the hydrogenation step.

8. A method of purifying an aromatic dicarboxylic acid according to claim 1, further comprising the step of, after the hydrogenation step, crystallizing the aromatic dicarboxylic acid.

9. A method of purifying an aromatic dicarboxylic acid according to claim 1, wherein the carbon monoxide is maintained at a concentration of 100 to 500 ppm, based on added hydrogen and carbon monoxide.

10. A method of purifying an aromatic dicarboxylic acid according to claim 1, wherein the carbon monoxide is maintained at a concentration of 10 to 1000 ppm based on added hydrogen and carbon monoxide.

11. A method of purifying an aromatic dicarboxylic acid according to claim 1, wherein the palladium catalyst is provided on a $TiO_2$ substrate.

12. A method of purifying an aromatic dicarboxylic acid, comprising the steps of:

oxidizing m-xylene or p-xylene to produce crude isophthalic acid, 3-carboxybenzaldehyde and fluorenones or crude terephthalic acid, 4-carboxylbenzaldehyde and fluorenones, respectively;

contacting the products of the oxidizing step with hydrogen in the presence of a palladium catalyst;

introducing carbon monoxide during the hydrogenation step, the amount of carbon monoxide introduced being less than or equal to 1000 ppm based on the added hydrogen and carbon monoxide; and monitoring the disappearance of 3-carboxybenzaldehyde in the case of oxidizing m-xylene and 4-carboxybenzaldehyde in the case of oxidizing p-xylene, and reducing the amount of carbon monoxide when the rate of disappearance is below a predetermined minimum.

13. A method of purifying an aromatic dicarboxylic acid according to claim 12, wherein the palladium catalyst is provided on a carbon substrate.

14. A method of purifying an aromatic dicarboxylic acid according to claim 12, wherein the products of the oxidizing step are dissolved in a solvent prior to the hydrogenation step.

15. A method of purifying an aromatic dicarboxylic acid according to claim 14, wherein water is used as the solvent.

16. A method of purifying an aromatic dicarboxylic acid according to claim 14, wherein the products of the oxidizing step are dissolved in a solvent at an elevated temperature, above the normal boiling point of the solvent.

17. A method of purifying an aromatic dicarboxylic acid according to claim 12, wherein the hydrogenation step hydrogenates the 3-carboxybenzaldehyde to m-toluic acid and 3-hydroxymethyl benzoic acid in the case of oxidizing m-xylene and hydrogenates the 4carboxybenzaldehyde to p-toluic acid and 4-hydroxymethyl benzoic acid in the case of oxidizing p-xylene.

18. A method of purifying an aromatic dicarboxylic acid according to claim 12, wherein the carbon monoxide is introduced intermittently during the hydrogenation step.

19. A method of purifying an aromatic dicarboxylic acid according to claim 12, further comprising the step of, after the hydrogenation step, crystallizing the isophthalic acid or terephthalic acid.

20. A method of purifying an aromatic dicarboxylic acid according to claim 12, wherein the carbon monoxide is maintained at a concentration of 100 to 500 ppm based on added hydrogen and carbon monoxide.

21. A method of purifying an aromatic dicarboxylic acid according to claim 12, wherein the carbon monoxide is maintained at a concentration of 10 to 1000 ppm based on added hydrogen and carbon monoxide.

22. A method of purifying an aromatic dicarboxylic acid according to claim 12, wherein the palladium catalyst is provided on a $TiO_2$ substrate.

23. A method of purifying an aromatic dicarboxylic acid, comprising the steps of:

oxidizing a dialkylaromatic to a crude aromatic dicarboxylic acid;

contacting the products of the oxidizing step with hydrogen in the presence of a palladium catalyst; and introducing carbon monoxide during the hydrogenation step, the amount of carbon monoxide introduced being less than or equal to 1000 ppm based on the added hydrogen and carbon monoxide, carbon monoxide being introduced intermittently during the hydrogenation step.

24. A method of purifying an aromatic dicarboxylic acid according to claim 23, wherein the palladium catalyst is provided on a carbon substrate.

25. A method of purifying an aromatic dicarboxylic acid according to claim 23, wherein the products of the oxidizing step are dissolved in a solvent prior to the hydrogenation step.

26. A method of purifying an aromatic dicarboxylic acid according to claim 25, wherein water is used as the solvent.

27. A method of purifying an aromatic dicarboxylic acid according to claim 25, wherein the products of the oxidizing step are dissolved in a solvent at an elevated temperature, above the normal boiling point of the solvent.

28. A method of purifying an aromatic dicarboxylic acid according to claim 25, wherein the oxidation step produces aromatic dicarboxylic acid-color bodies and an aromatic carboxylic acid aldehyde; and the hydrogenation step hydrogenates the aromatic carboxylic acid aldehyde to an aromatic alkyl carboxylic acid and an aromatic alcohol carboxylic acid.

29. A method of purifying an aromatic dicarboxylic acid according to claim 23, further comprising the step of, after the hydrogenation step, crystallizing the aromatic dicarboxylic acid.

30. A method of purifying an aromatic dicarboxylic acid according to claim 23, wherein the carbon monoxide is maintained at a concentration of 100 to 500 ppm, based on added hydrogen and carbon monoxide.

31. A method of purifying an aromatic dicarboxylic acid according to claim 23, wherein the carbon monoxide is maintained at a concentration of 10 to 1000 ppm based on added hydrogen and carbon monoxide.

32. A method of purifying an aromatic dicarboxylic acid according to claim 23, wherein the palladium catalyst is provided on a $TiO_2$ substrate.

33. A method of purifying an aromatic dicarboxylic acid, comprising the steps of:
   oxidizing a dialkylaromatic to a crude aromatic dicarboxylic acid to produce crude isophthalic acid or crude terephthalic acid, respectively;
   contacting the products of the oxidizing step with hydrogen in the presence of a palladium catalyst; and
   introducing carbon monoxide during the hydrogenation step, the amount of carbon monoxide introduced being maintained at a concentration of 100 to 500 ppm based on the added hydrogen and carbon monoxide.

34. A method of purifying an aromatic dicarboxylic acid according to claim 33, wherein the palladium catalyst is provided on a carbon substrate.

35. A method of purifying an aromatic dicarboxylic acid according to claim 33, wherein the products of the oxidizing step are dissolved in a solvent prior to the hydrogenation step.

36. A method of purifying an aromatic dicarboxylic acid according to claim 33, wherein water is used as the solvent.

37. A method of purifying an aromatic dicarboxylic acid according to claim 35, wherein the products of the oxidizing step are dissolved in a solvent at an elevated temperature, above the normal boiling point of the solvent.

38. A method of purifying an aromatic dicarboxylic acid according to claim 33, wherein the oxidation step produces aromatic dicarboxylic acid-color bodies and an aromatic carboxylic acid aldehyde.

39. A method of purifying an aromatic dicarboxylic acid according to claim 38, wherein the hydrogenation step hydrogenates the aromatic carboxylic acid aldehyde to an aromatic alkyl carboxylic acid and an aromatic alcohol carboxylic acid.

40. A method of purifying an aromatic dicarboxylic acid according to claim 33, further comprising the step of, after the hydrogenation step, crystallizing the aromatic dicarboxylic acid.

41. A method of purifying an aromatic dicarboxylic acid according to claim 33, wherein the palladium catalyst is provided on a $TiO_2$ substrate.

42. A method of purifying an aromatic dicarboxylic acid, comprising the steps of:
   oxidizing m-xylene or p-xylene to produce crude isophthalic acid or crude terephthalic acid, respectively;
   contacting the products of the oxidizing step with hydrogen in the presence of a palladium catalyst; and
   introducing carbon monoxide during the hydrogenation step, the amount of carbon monoxide introduced being less than or equal to 1000 ppm based on the added hydrogen and carbon monoxide, carbon monoxide being introduced intermittently during the hydrogenation step.

43. A method of purifying an aromatic dicarboxylic acid according to claim 42, wherein the palladium catalyst is provided on a carbon substrate.

44. A method of purifying an aromatic dicarboxylic acid according to claim 42, wherein the products of the oxidizing step are dissolved in a solvent prior to the hydrogenation step.

45. A method of purifying an aromatic dicarboxylic acid according to claim 44, wherein water is used as the solvent.

46. A method of purifying an aromatic dicarboxylic acid according to claim 44, wherein the products of the oxidizing step are dissolved in a solvent at an elevated temperature, above the normal boiling point of the solvent.

47. A method of purifying an aromatic dicarboxylic acid according to claim 42, wherein the oxidation step produces isophthalic acid, 3-carboxybenzaldehyde and fluorenones in the case of oxidizing m-xylene and produces terephthalic acid, 4-carboxybenzaldehyde and fluorenones in the case of oxidizing p-xylene; and
   the hydrogenation step hydrogenates the 3-carboxybenzaldehyde to m-toluic acid and 3-hydroxymethyl benzoic acid in the case of oxidizing m-xylene and hydrogenates the 4-carboxybenzaldehyde to p-toluic acid and 4-hydroxymethyl benzoic acid in the case of oxidizing p-xylene.

48. A method of purifying an aromatic dicarboxylic acid according to claim 42, further comprising the step of, after the hydrogenation step, crystallizing the isophthalic acid or terephthalic acid.

49. A method of purifying an aromatic dicarboxylic acid according to claim 42, wherein the carbon monoxide is maintained at a concentration of 100 to 500 ppm based on added hydrogen and carbon monoxide.

50. A method of purifying an aromatic dicarboxylic acid according to claim 42, wherein the carbon monoxide is maintained at a concentration of 10 to 1000 ppm based on added hydrogen and carbon monoxide.

51. A method of purifying an aromatic dicarboxylic acid according to claim 42, wherein the palladium catalyst is provided on a $TiO_2$ substrate.

52. A method of purifying an aromatic dicarboxylic acid, comprising the steps of:
   oxidizing m-xylene or p-xylene to produce crude isophthalic acid or crude terephthalic acid, respectively;
   contacting the products of the oxidizing step with hydrogen in the presence of a palladium catalyst; and
   introducing carbon monoxide during the hydrogenation step, the amount of carbon monoxide introduced being maintained at a concentration of 100 to 500 ppm based on the added hydrogen and carbon monoxide.

53. A method of purifying an aromatic dicarboxylic acid according to claim 52, wherein the palladium catalyst is provided on a carbon substrate.

54. A method of purifying an aromatic dicarboxylic acid according to claim 52, wherein the products of the oxidizing step are dissolved in a solvent prior to the hydrogenation step.

55. A method of purifying an aromatic dicarboxylic acid according to claim 54, wherein water is used as the solvent.

56. A method of purifying an aromatic dicarboxylic acid according to claim 54, wherein the products of the oxidizing step are dissolved in a solvent at an elevated temperature, above the normal boiling point of the solvent.

57. A method of purifying an aromatic dicarboxylic acid according to claim 52, wherein the oxidation step produces isophthalic acid, 3-carboxybenzaldehyde and fluorenones in the case of oxidizing m-xylene and produces terephthalic acid, 4-carboxybenzaldehyde and fluorenones in the case of oxidizing p-xylene.

58. A method of purifying an aromatic dicarboxylic acid according to claim 57, wherein the hydrogenation step hydrogenates the 3-carboxybenzaldehyde to m-toluic acid and 3-hydroxymethyl benzoic acid in the case of oxidizing m-xylene and hydrogenates the 4-carboxybenzaldehyde to p-toluic acid and 4-hydroxymethyl benzoic acid in the case of oxidizing p-xylene.

59. A method of purifying an aromatic dicarboxylic acid according to claim 52, further comprising the step of, after the hydrogenation step, crystallizing the isophthalic acid or terephthalic acid.

60. A method of purifying an aromatic dicarboxylic acid according to claim 52, wherein the palladium catalyst is provided on a $TiO_2$ substrate.

61. A method of purifying an aromatic dicarboxylic acid, comprising the steps of:

oxidizing a dialkylaromatic to a crude aromatic dicarboxylic acid having impurities;

contacting the products of the oxidizing step with hydrogen in the presence of a palladium catalyst to hydrogenate the impurities; and introducing carbon monoxide during the hydrogenation step, the amount of carbon monoxide introduced being less than or equal to 1000 ppm based on the added hydrogen and carbon monoxide.

* * * * *

UNITED STATES PATENT AND TRADEMARK OFFICE
CERTIFICATE OF CORRECTION

PATENT NO. : 6,265,608 B1  
DATED : July 24, 2001  
INVENTOR(S) : Charles E. Sumner, Jr. et al.

Page 1 of 1

It is certified that error appears in the above-identified patent and that said Letters Patent is hereby corrected as shown below:

<u>Column 4,</u>
Line 65, delete paragraph break; and

<u>Column 8,</u>
Line 11, before "4" enter -- - -- (a hyphen).

Signed and Sealed this

Seventh Day of May, 2002

Attest:

JAMES E. ROGAN  
*Director of the United States Patent and Trademark Office*

*Attesting Officer*

UNITED STATES PATENT AND TRADEMARK OFFICE
CERTIFICATE OF CORRECTION

PATENT NO. : 6,265,608 B1 Page 1 of 1
DATED : July 24, 2001
INVENTOR(S) : Charles E. Sumner, Jr. et al.

It is certified that error appears in the above-identified patent and that said Letters Patent is hereby corrected as shown below:

<u>Column 2,</u>
Line 45, change "fluorenone" to -- fluorene --.

Signed and Sealed this

Twenty-fifth Day of February, 2003

JAMES E. ROGAN
*Director of the United States Patent and Trademark Office*